United States Patent
Kang et al.

(10) Patent No.: US 10,398,355 B2
(45) Date of Patent: Sep. 3, 2019

(54) SMART BELT AND CONTROL METHOD THEREOF

(71) Applicant: WELT CORP., LTD., Seoul (KR)

(72) Inventors: Seong Ji Kang, Seoul (KR); Hye Kang Roh, Seoul (KR)

(73) Assignee: WELT CORP., LTD., Seoul (KR)

( * ) Notice: Subject to any disclaimer, the term of this patent is extended or adjusted under 35 U.S.C. 154(b) by 258 days.

(21) Appl. No.: 15/266,762

(22) Filed: Sep. 15, 2016

(65) Prior Publication Data

US 2018/0035917 A1    Feb. 8, 2018

(30) Foreign Application Priority Data

Aug. 5, 2016 (KR) .................. 10-2016-0099968

(51) Int. Cl.
| | |
|---|---|
| *A61B 5/107* | (2006.01) |
| *A41F 9/00* | (2006.01) |
| *A61B 5/00* | (2006.01) |
| *A61B 5/05* | (2006.01) |
| *A61B 5/11* | (2006.01) |

(Continued)

(52) U.S. Cl.
CPC ............ *A61B 5/1072* (2013.01); *A41F 9/002* (2013.01); *A61B 5/05* (2013.01); *A61B 5/1077* (2013.01); *A61B 5/11* (2013.01); *A61B 5/1126* (2013.01); *A61B 5/6804* (2013.01); *A61B 5/6823* (2013.01); *A61B 5/6831* (2013.01); *A61B 5/6838* (2013.01); *A61B 5/6843* (2013.01); *G01B 7/046* (2013.01); *G01L 1/2287* (2013.01); *G06F 1/163* (2013.01); *A41H 1/02* (2013.01); *A61B 5/1114* (2013.01)

(58) Field of Classification Search
CPC ......... A41F 9/002; A61B 5/05; A61B 5/1007; A61B 5/11
See application file for complete search history.

(56) References Cited

U.S. PATENT DOCUMENTS

| | | | |
|---|---|---|---|
| 2009/0234201 A1 | 9/2009 | Huang et al. | |
| 2013/0215116 A1* | 8/2013 | Siddique | G06Q 30/0643 345/420 |

(Continued)

FOREIGN PATENT DOCUMENTS

| | | |
|---|---|---|
| CN | 203849843 U | 9/2014 |
| CN | 104127184 A | 11/2014 |

(Continued)

*Primary Examiner* — Richale L Quinn
(74) *Attorney, Agent, or Firm* — Rabin & Berdo, P.C.

(57) ABSTRACT

A smart belt and a control method thereof are provided, in which a belt device is provided, including a strap portion comprising a plurality of magnet patterns, a first sensor portion configured to sense one of the plurality of magnet patterns while the strap portion is being fastened to a buckle portion, and a controller configured to obtain a length of a waist circumference of a user that corresponds to the magnet pattern sensed by the first sensor portion. The belt apparatus may additionally include a clip portion connecting the strap portion with the buckle portion, and a second sensor portion configured to measure a tension exerted on the clip portion while the strap portion is being fastened to the buckle portion. The controller may correct the length of the waist circumference using a waist circumference correction value corresponding to the measured tension.

7 Claims, 5 Drawing Sheets

(51) Int. Cl.
*G01B 7/04* (2006.01)
*G01L 1/22* (2006.01)
*G06F 1/16* (2006.01)
*A41H 1/02* (2006.01)

(56) References Cited

U.S. PATENT DOCUMENTS

| | | | |
|---|---|---|---|
| 2016/0153853 A1* | 6/2016 | Brenner | G01L 5/047 702/155 |
| 2016/0302724 A1* | 10/2016 | Coulm | A44B 11/005 |
| 2017/0055881 A1* | 3/2017 | Kang | A61B 5/002 |
| 2017/0205801 A1* | 7/2017 | Manning | G05B 19/402 |
| 2018/0256074 A1* | 9/2018 | Persidsky | A61B 5/113 |

FOREIGN PATENT DOCUMENTS

| | | |
|---|---|---|
| JP | S63-175121 A | 7/1988 |
| JP | 2000-155037 A | 6/2000 |
| JP | 2015-188675 A | 11/2015 |
| KR | 20-0241939 Y1 | 9/2001 |
| KR | 10-009-0094554 A | 9/2009 |
| KR | 10-2010-0021854 A | 2/2010 |
| KR | 10-0964976 B1 | 6/2010 |
| KR | 10-2016-0082939 A | 7/2016 |
| WO | WO 2010-021441 A1 | 2/2010 |

\* cited by examiner

SMART BELT AND CONTROL METHOD THEREOF

CROSS-REFERENCE TO RELATED APPLICATIONS

This application claims priority from Korean Patent Application No. 10-2016-0099968, filed on Aug. 5, 2016 in the Korean Intellectual Property Office, the disclosure of which is incorporated herein by reference in its entirety.

BACKGROUND

1. Field of the Invention

The present disclosure relates to a smart belt capable of measuring a length of a waist circumference of a user, and a control method thereof.

2. Description of the Related Art

Wearable device is a device that can be worn on a user. Active researches on wearable devices have enabled launching of a diverse forms of wearable devices into the market. Currently available wearable devices include glasses, bands, watches, shoes, and so on. For the characteristic of being 'wearable on a body,' the wearable devices are widely applied in the healthcare field. One example is a wearable band, which can check and record user's amount of exercise, sleep time, quality of sleep, and so on.

Meanwhile, recent papers have presented that the increased waist size results in decreased thickness of cerebral cortex, which subsequently leads into increased risk of dementia. It was also revealed that, for men, the risk of having colorectal cancer increases by 33% with every 3.3-inch increase above 35-inch reference. Accordingly, it is necessary to develop a wearable device that is capable of accurately measuring a length of waist circumference as it is in close relationship with the health.

SUMMARY

Exemplary embodiments of the present inventive concept overcome the above disadvantages and other disadvantages not described above. Also, the present inventive concept is not required to overcome the disadvantages described above, and an exemplary embodiment of the present inventive concept may not overcome any of the problems described above.

According to an embodiment, a technical objective is to provide a smart belt capable of accurately measuring a length of waist circumference of a user wearing the same, and a control method thereof.

In order achieve the technical objectives of the present disclosure, according to an exemplary embodiment, a belt apparatus is provided, which may include a strap portion comprising a plurality of magnet patterns, a first sensor portion configured to sense one of the plurality of magnet patterns while the strap portion is being fastened to a buckle portion, and a controller configured to obtain a length of a waist circumference of a user that corresponds to the magnet pattern sensed by the first sensor portion.

The belt apparatus may additionally include a clip portion connecting the strap portion with the buckle portion, and a second sensor portion configured to measure a tension exerted on the clip portion while the strap portion is being fastened to the buckle portion. The controller may correct the length of the waist circumference using a waist circumference correction value corresponding to the measured tension.

The strap portion may include a plurality of holes corresponding to the plurality of magnet patterns, respectively.

Lengths of the waist circumference of the user corresponding to the magnet patterns may be determined based on distances from predetermined points of the buckle portion or the clip portion to the holes that correspond to the plurality of magnet patterns, respectively.

The first sensor portion may include a magnetic sensor.

The second sensor portion may include a strain gauge or a force sensing resistor (FSR) sensor.

The clip portion may include a body portion comprising an attachment surface on which the strain gauge or the FSR sensor is attached, and a cover portion comprising an electromagnetic transmitting window configured to allow the magnetic sensor to sense a magnetic signal generated from the magnet pattern, among the plurality of magnet patterns, that is positioned above the clip portion.

An electromagnetic permeable plate may be attached on an outer side of the cover portion.

The belt apparatus may additionally include a third sensor portion configured to sense user motion information of a user wearing the belt apparatus.

The controller may correct the tension using the user motion information sensed at the third sensor portion.

The controller may measure the length of the waist circumference of the user in a predetermined state, based on the user motion information.

The belt apparatus may additionally include a memory configured to store a table composed of a waist circumference correction value corresponding to the measured tension.

The plurality of magnet patterns may be distinguished from one another according to at least one of: a number of magnets included in the magnet patterns; positions of the magnets; polarities of the magnets; and intensities of the magnets.

In order to achieve the technical objectives, according to another exemplary embodiment, a belt apparatus is provided, which may include a buckle portion, a strap portion comprising a plurality of magnet patterns, and a plurality of holes corresponding to the plurality of magnet patterns, respectively, and a clip portion connecting the strap portion to the buckle portion.

The clip portion may include a body portion including an attachment surface formed thereon to which a tension sensor to measure a tension exerted on the clip portion is attached, and a cover portion including an electromagnetic transmitting window formed thereon to allow a magnetic sensor to sense a magnetic signal generated from a magnet pattern, among the plurality of magnet patterns, that is positioned above the clip portion.

In order to achieve the technical objectives, according to another exemplary embodiment, a control method of a belt apparatus, which may include, while a strap portion having a plurality of magnet patterns formed thereon is being fastened to a buckle portion, sensing one of the plurality of magnet patterns, obtaining a length of a waist circumference of a user corresponding to the sensed magnet pattern, and correcting the length of the waist circumference to a waist circumference correction value corresponding to the measured tension.

According to various exemplary embodiments, it is possible to automatically measure a length of a user's waist circumference with accuracy.

BRIEF DESCRIPTION OF THE DRAWINGS

The above and/or other aspects of the present inventive concept will be more apparent by describing certain exemplary embodiments of the present inventive concept with reference to the accompanying drawings, in which.

DETAILED DESCRIPTION OF EXEMPLARY EMBODIMENTS

Certain exemplary embodiments of the present inventive concept will now be described in greater detail with reference to the accompanying drawings.

Figure 1:
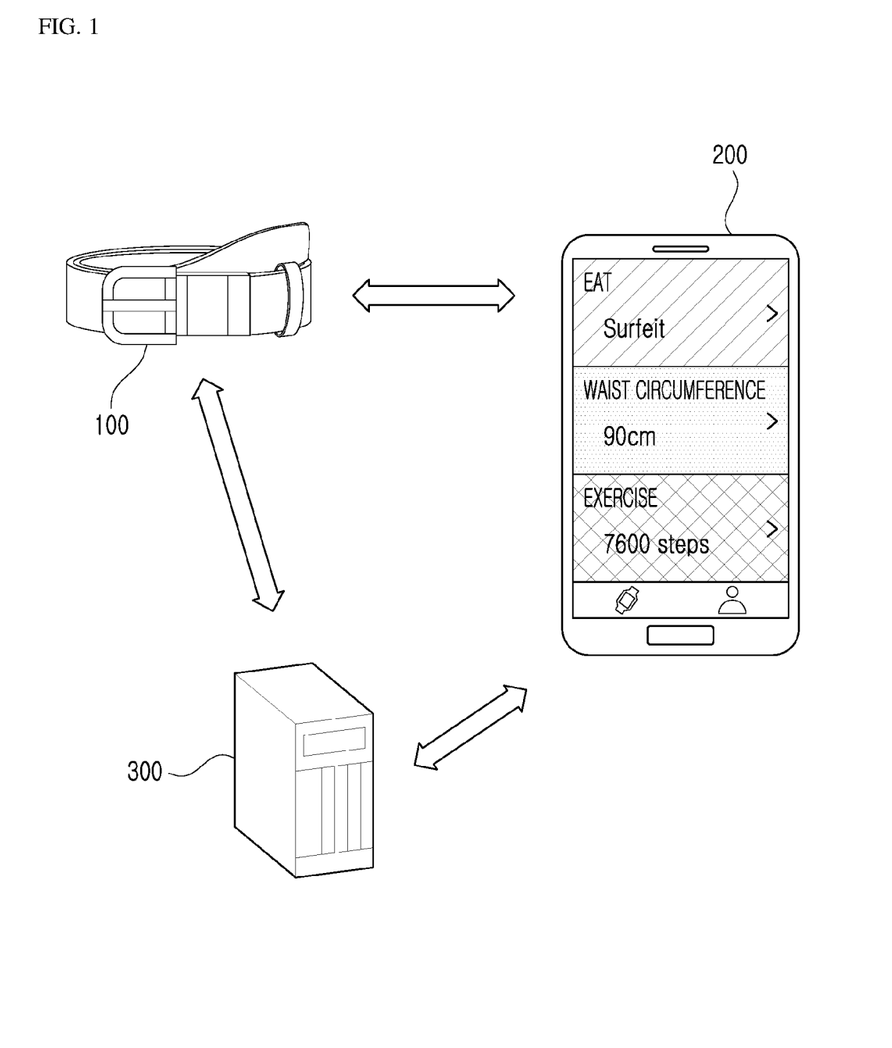
FIG. 1 is a view provided to explain a waist circumference management system according to an exemplary embodiment.

FIG. 1 is a view provided to explain a waist circumference management system according to an exemplary embodiment.

Referring to FIG. 1, a waist circumference management system according to an exemplary embodiment may include a smart belt 100, a host terminal 200, and a server 300. Of course, the waist circumference management system according to an exemplary embodiment may be implemented with only the smart belt 100 and the host terminal 200. Of course, the waist circumference management system according to an exemplary embodiment may be implemented with the smart belt 100 only.

The smart belt 100 may be a device that can measure a length of waist circumference of a user. The smart belt 100 may be worn on the waist of the user. The smart belt 100 may provide a function to keep trousers or skirts worn on the user from sliding down. The smart belt 100 may be implemented in a variety of forms and with a variety of materials.

The smart belt 100 may sense the presence or absence of the smart belt 100 worn on the user, detect a movement of the user, measure a length of waist circumference of the user, or measure a tension exerted to the smart belt 100, using at least one sensor. The 'tension' herein may refer to a force at an arbitrary plane within an object, which vertically pulls apart two sides with reference to the plane. Further, the smart belt 100 may correct the waist circumference measurement according to the tension of the smart belt 100.

The smart belt 100 may communicate with an external device via communication networks. According to an exemplary embodiment, the communication network may be implemented with a wireless communication technology, such as, wireless fidelity (Wi-Fi), home RF, Bluetooth, HR WPAN, UWB, LR WPAN, IEEE 1394, and so on, but not limited thereto.

For example, the smart belt 100 may transmit information associated with the waist circumference to the host terminal 200. Further, the smart belt 100 may transmit tension information, breathing information, overeating information of the user, user's motion information, and so on, to the host terminal 200. Further, the smart belt 100 may transmit to the host terminal 200 the user's activity information, such as, information on user's commuting to and from office, overworking, use of restrooms, total time of sitting, seizure or fall-accident, smoking, laughing, and so on.

The host terminal 200 may be a device that includes a display that can output information. The host terminal 200 may output a variety of information transmitted from the smart belt 100 or the server 300. For example, the host terminal 200 may output notification or warning messages based on the health-related information regarding the user (e.g., waist circumference-related information) transmitted from the smart belt 100.

Further, the host terminal 200 may itself generate the length of the user's waist circumference, user's activity information, and so on, based on the information transmitted from the smart belt 100. According to an exemplary embodiment, the host terminal 200 may be implemented in a variety of forms. For example, the host terminal 200 may be digital camera, smart phone, laptop computer, tablet PC, e-book terminal, digital broadcast terminal, PDA, portable multimedia player (PMP), navigation, MP3 player, and so on, but not limited thereto. The host terminal 200 as described herein may refer to a device that can be worn by the user. The wearable device may include at least one of accessory type device (e.g., watch, ring, bracelet, ankle bracelet, necklace, glasses, contact lens), head-mounted-device (HMD), fabric or cloth-integrated device (e.g., electronic clothes), body-attached device (e.g., skin pad), or biologically-implantable device (implantable circuit).

The user may check his or her health status by checking the information on the waist circumference (or 'waist circumference information' hereinbelow for convenience of explanation) as displayed on the host terminal 200. The waist circumference is the prerequisite for the determination of the metabolic syndrome, and used as a more important factor than the body mass index (BMI) when determining obesity. Accordingly, a system is necessary, which can provide accurate waist circumference information to the user and manage the waist circumference information of the user.

The server 300 is provided to transmit and receive data to and from the smart belt 100 and the host terminal 200. For example, the server 300 may be one of a cloud server, a personalized server, a medical institute server, and a health information storage server. The health information storage server may include electronic medical record (EMR) server, electronic health record (HER) server, personal health record (PHR) server, and so on, but not limited thereto.

The server 300 may analyze the information measured at the smart belt 100 such as the waist circumference information, the user's motion information, the tension information, and so on, through an intelligence engine. For example, the server 300 may correct the waist circumference based on the tension information of the smart belt 100, or determine risk of abdominal obesity and/or metabolic syndrome based on the corrected waist circumference information.

Figure 2:
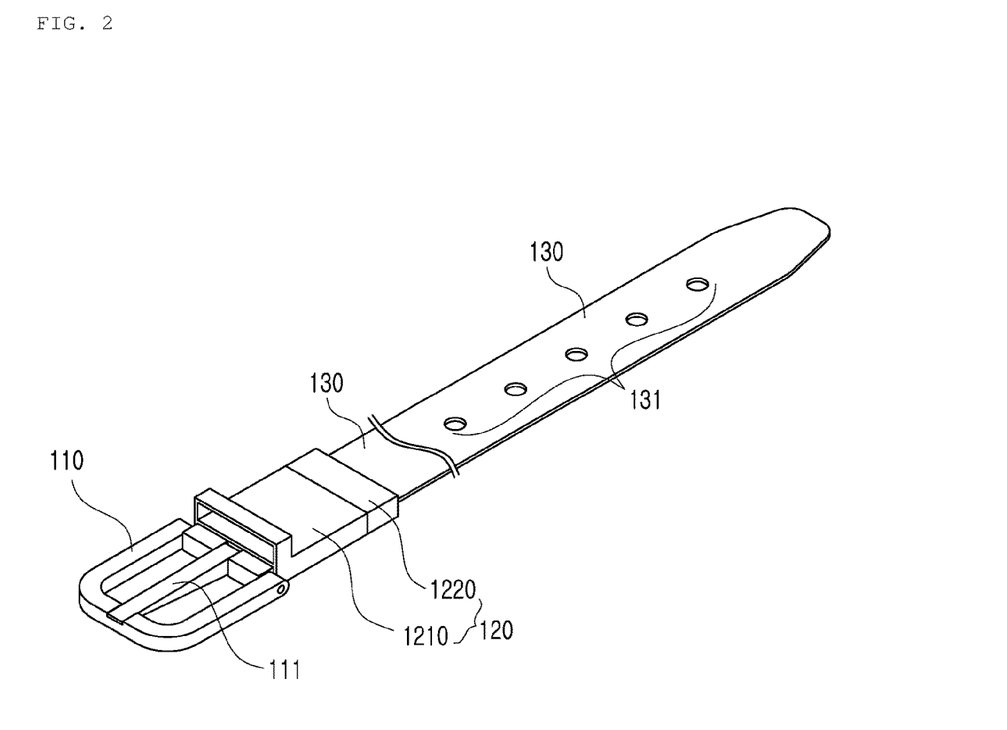
FIG. 2 is a view provided to explain a smart belt according to an exemplary embodiment.

FIG. 2 is a view provided to explain a smart belt according to an exemplary embodiment.

Referring to FIG. 2, the smart belt 100 may include a buckle portion 110, a clip portion 120, and a strap portion 130.

The buckle portion 110 may include an apparatus for fastening the strap portion 130. The buckle portion 110 may be implemented as a variety of forms such as cinch buckle, ring buckle, plate buckle, rectangular buckle, clasp buckle, frame buckles, trench buckle, and so on.

The buckle portion 110 exemplified in FIG. 2 may include a fin-shaped fastening portion 111 to be fit in any of a plurality of holes 131 formed in the strap portion 130 to fasten the strap portion 130.

The clip portion 120 is provided to connect the buckle portion 110 with the strap portion 130 and may house therein electronic components of the smart belt 100.

The clip portion 120 may include a cover portion 1210 and a body portion 1220.

The body portion 1220 is provided to connect the buckle portion 110 with the strap portion 130, and to mount the electronic components thereon. The electronic components of the smart belt 100 may include a magnetic sensor, a tension sensor, an inertial sensor, a processor, a memory, a battery, a communication interface, and so on.

The cover portion 1210 has a structure to cover the body 1220 having the electronic components mounted thereon.

The strap portion 130 may be implemented as a form of a strap and formed from a variety of materials including leather, fabric, and so on.

The strap portion 130 may include a plurality of holes 131 formed therein. The fastening portion 111 may be fit in one of a plurality of holes 131 such that the circumference of the smart belt 100 may be adjusted to the waist circumference of the user. The circumference of the smart belt 100 herein refers to a distance spanning from the hole into which the fastening portion 111 is fit and back to the same hole, while the user is wearing the smart belt 100.

The strap portion 130 may include a plurality of magnet patterns (not illustrated).

Figure 3:
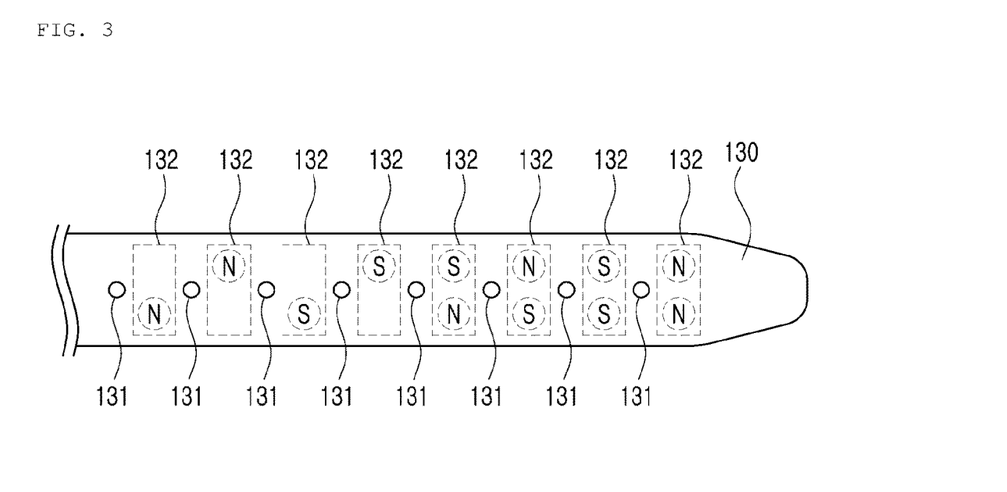
FIG. 3 is a view provided to explain a plurality of magnet patterns formed on a strap portion according to an exemplary embodiment.
Figure 4:
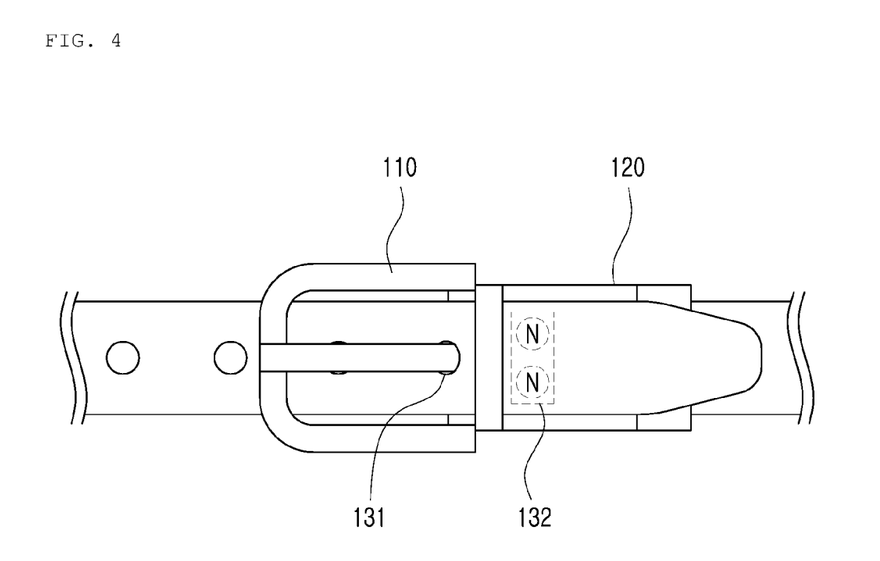
FIG. 4 is a view provided to explain sensing a magnet pattern corresponding to a hole, according to an exemplary embodiment.

FIG. 3 is a view provided to explain a plurality of magnet patterns formed on the strap portion according to an exemplary embodiment, and FIG. 4 is a view provided to explain sensing magnet pattern corresponding to a hole, according to an exemplary embodiment.

Referring to FIG. 3, a plurality of magnet patterns 132 may be positioned within the strap portion 130 such that the magnet patterns 132 are hidden from view. The plurality of magnet patterns 132 may be distinguished from one another according to a number of magnets included in the corresponding magnet pattern, positions of the magnets, polarities and intensities of the magnets.

Meanwhile, a plurality of holes 131 may be formed at predetermined intervals along a lengthwise direction of the strap portion 130. Likewise, a plurality of magnet patterns 132 may also be formed at predetermined intervals along the lengthwise direction of the strap portion 130. The intervals among the plurality of holes and the intervals among the plurality of magnet patterns 132 may be same as each other.

FIG. 3 illustrates an example in which a plurality of magnet patterns 132 include two magnets or one magnet, respectively, but with different combinations of magnet polarities and magnet positions such that the magnet patterns are distinguished from one another.

Of course, there may be three of more magnets included in one magnet pattern, or alternately, the number of magnets may be limited to 1. The position where the magnets are disposed may also be different from the positions exemplified in FIG. 3. Meanwhile, when a magnetic sensor is able to distinguish the intensities of the magnets by levels, an implementation may be contemplated, according to which a magnet pattern is distinguished from other magnet patterns by varying a combination of intensity levels of the magnets included in the magnet patterns.

A plurality of holes 131 and a plurality of magnet patterns 132 may be disposed in the strap portion 130 in a manner in which the holes and the corresponding magnet patterns are at predetermined intervals from one another. For example, when the fastening portion 111 is fit into the hole (i.e., the right-most hole in FIG. 3) located at the end of the strap portion 130, as exemplified in FIG. 4, the magnet patterns composed of two N-poles corresponding to that hole may be located at the clip portion 120.

According this configuration, it is possible to determine the hole 131, among a plurality of holes 131, the fastening portion 111 is being fit into, as the magnetic sensor received in the clip portion 120 senses the magnet pattern located at the clip portion 120. Of course, it may be determined that the user is not wearing the smart belt 100, if the magnet pattern is not sensed by the magnetic sensor.

Of course, according to exemplary embodiments, the magnetic sensor may be disposed not at the clip portion 120, but at the buckle portion 110, or at a portion of the strap portion 130. In this example too, the interval between the hole and the magnet pattern may be determined such that the magnet pattern corresponding to a hole having the fastening portion 111 fit therein, is located above the magnetic sensor.

Meanwhile, according to an exemplary embodiment, both surfaces of the strap portion 130 may have different colors or designs such that the user can use the two surfaces of the strap portion 130 alternately. In this case, the magnetic pattern is reversed when either of the two surfaces of the strap portion 130 that is used as the outer surface is changed. For example, the magnet pattern including two N-pole magnets on one surface of the strap portion 130 may be recognized on the other surface as a magnet pattern having two S-pole magnets.

Accordingly, there is no overlap between the magnet patterns recognized on one surface of the strap portion 130, and the magnet patterns recognized on the other surface. Additionally, the magnet patterns on one surface and the magnet patterns on the other surface may be paired with each other to correspond to each of the holes of the strap portion 130. In this manner, it is possible to recognize the hole that has the fastening portion 111 fitted therein, regardless of whether the outer surface is the one surface of the strap portion 130 or the other.

Meanwhile, according to exemplary embodiments, a sensor (not illustrated) may be additionally provided to sense both surfaces of the strap portion 130, in which case it is possible to determine whether the outer surface of the strap portion 130 is one surface or the other, and accordingly recognize a hole that corresponds to the sensed magnet pattern. For example, a magnet that can recognize both surfaces may be formed on one end of the strap portion 130, and it may be determined, through a separate sensor provided on the clip portion 120, which of the surfaces of the strap portion 130 is the outer surface. Of course, other methods may be contemplated.

Figure 5:
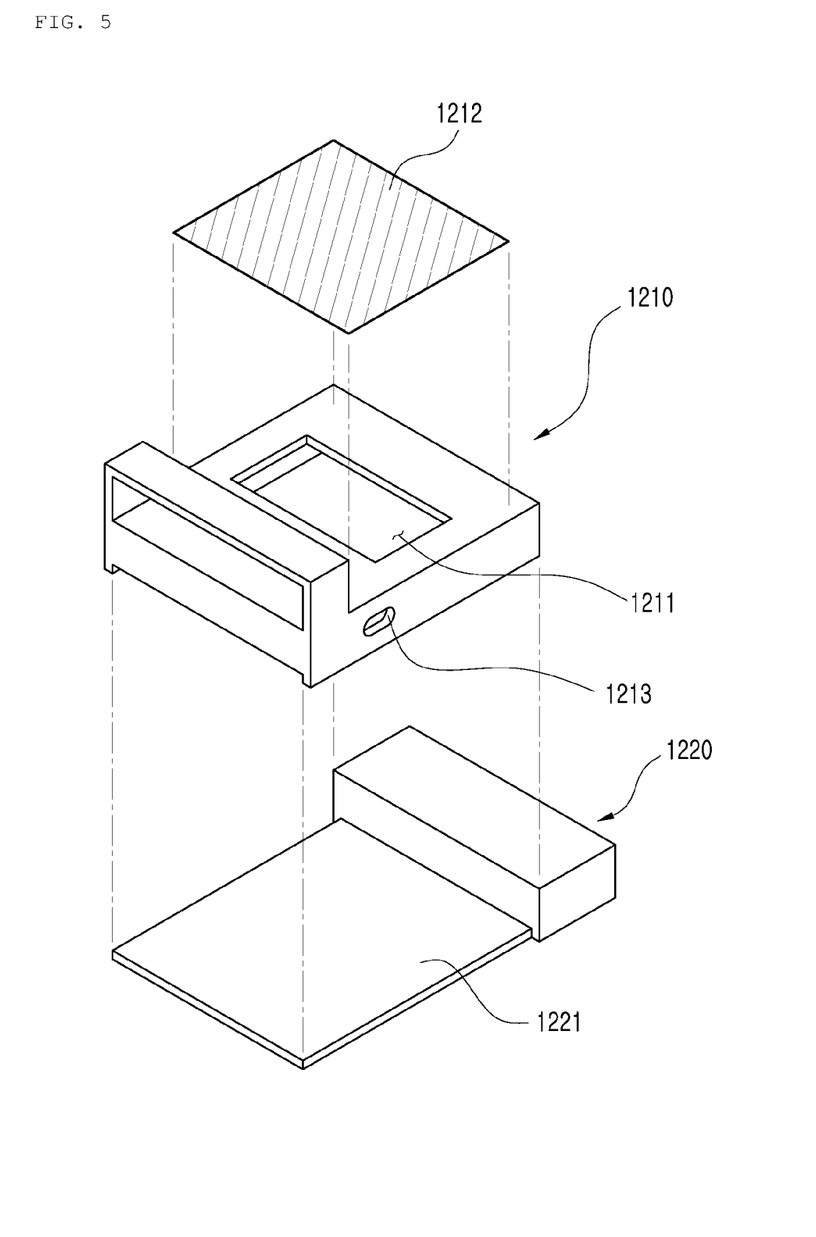
FIG. 5 illustrates a detailed configuration of a clip portion of a smart belt according to an exemplary embodiment.

FIG. 5 illustrates a detailed configuration of a clip portion of a smart belt according to an exemplary embodiment.

Referring to FIG. 5, the body portion 1220 may include an attachment surface 1221 where a tension sensor (not illustrated) is attached. The tension sensor may be implemented as a strain gauge or a force sensing resistor (FSR) sensor, but not limited thereto.

The strain gauge can measure the strain of an object, using a characteristic in which the electrical resistance changes when the object experiences deformation. The FSR sensor can measure dynamic force (e.g., tension) using the resistance changed by the force or pressure exerted on the surface.

The tension sensor attached to the attachment surface 1221 can measure the tension exerted on the smart belt 100 or the variations in the tension. For example, while the user is wearing the smart belt 100, when the tension is exerted on the smart belt 100, minute deformation may be occurred on the body portion 1220. The strain gauge or the FSR sensor attached to the attachment surface 1221 can sense the deformation occurring on the attachment surface 1221 to thus measure the tension exerted on the smart belt 100 or the variations in the tension.

The cover portion 1210 and the body portion 1221 may be formed from a metal material for the sake of durability. Meanwhile, a metallic object shields electric waves and magnetic components. Accordingly, in order to allow the magnetic sensor positioned above the clip portion 120 to sense the magnet pattern and to communicate externally, the cover portion 1210 may include an electromagnetic transmitting window 1211.

The electromagnetic transmitting window 1211 may be configured in a form of a hole in the cover portion 1210. Additionally, an electromagnetic permeable plate 1212 may be attached to the outer side of the cover portion 1210 to prevent exposure of the internal electronic components to outside.

Of course, according to exemplary embodiments, the electromagnetic transmitting window 1211 made from an electromagnetic permeable material may be formed at a portion of the cover portion 1210.

According to an exemplary embodiment, the cover portion 1210 may include a port hole 1213 for charging or data input and output. For example, the smart belt 100 may charge an internal battery through Micro 5-pin USB port.

Figure 6:
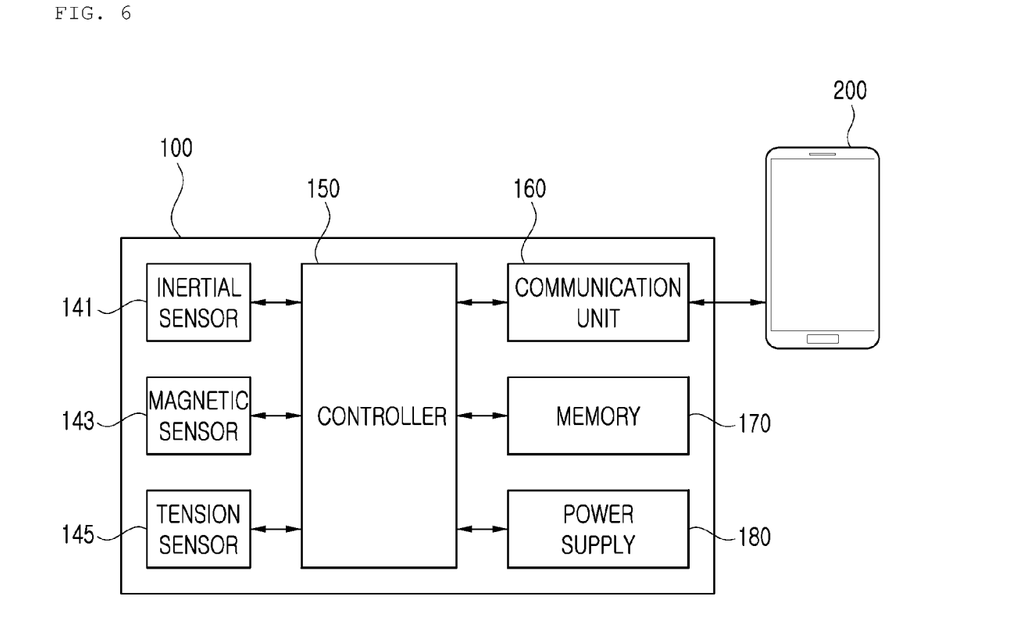
FIG. 6 is a view provided to explain electronic components of a smart belt according to an exemplary embodiment.

FIG. 6 is a view provided to explain electronic components of the smart belt according to an exemplary embodiment.

Referring to FIG. 6, the smart belt 100 may include an inertial sensor (IMU sensor) 141, a magnetic sensor 143, a tension sensor 145, a controller 150, a communication unit 160, a memory 170, and a power supply 180, although not all the components illustrated herein are essential components. Accordingly, the smart belt 100 may be realized with more components than those illustrated herein, or alternatively, the smart belt 100 may be realized with less components than those illustrated herein.

The inertial sensor (IMU sensor) 141 may include at least one of an acceleration sensor, a gyro sensor, and a geomagnetic sensor, and may measure a movement or a posture of an object.

According to an exemplary embodiment, the inertial sensor 141 may acquire user motion information. The user motion information may relate to a movement of the user wearing the smart belt 100. For example, the user motion information may include at least one of information on moving speed of the user, moving direction of the user, or tilting of the user, but not limited thereto. The user motion information may include biometric information (e.g., body temperature, breathing, amount of sweat, and so on), position information of the user (e.g., GPS coordinate value information, area information, building information, displacement made for a predetermined time, and so on). The biometric information of the user, and the position information of the user may be measured by a sensor other than the inertial sensor 141.

When acquiring the user motion information, the inertial sensor 141 may transmit the user motion information to the controller 150.

When the user is wearing the smart belt 100, the magnetic sensor 143 performs the function to sense one of a plurality of magnet patterns 132 formed on the strap portion 130. To this purpose, the magnetic sensor 143 may be implemented as a Hall sensor. Of course, a different type of magnetic sensor other than the Hall sensor may be used as well, as long as it can sense the magnet patterns. The number of the Hall sensors may be equal to the maximum number of magnets that can be included in the magnet patterns.

The magnetic sensor 143 may transmit the sensed magnet pattern information to the controller 150.

The tension sensor 145 may be provided to measure the tension exerted on the smart belt 100 or variations in the tension. The tension sensor 145 may include FSR sensor or strain gauge, but not limited thereto.

The tension sensor 145 may be attached onto the attachment surface 1221 formed on the body portion 1220 of the clip portion 120. Of course, the tension sensor 145 may be attached to other location of the smart belt 100 as long as it can measure the tension exerted on the smart belt 100.

When the tension exerted on the smart belt 100 is measured, the tension sensor 145 may transmit the information on the measured tension to the controller 150.

The controller 150 may drive operating system or application programs to control a plurality of hardware or software components connected to the controller 150, and perform processing and operation of various data.

For example, the controller 150 may obtain the length of the user's waist circumference, using the information acquired from the inertial sensor 141, the magnetic sensor 143, and the tension sensor 145. Further, the controller 150 may control the communication unit 160 to exchange respective data associated with the waist circumference length with the external host terminal 200.

As exemplified in FIG. 2, when a plurality of holes 131 are formed in the strap portion 130 at predetermined intervals, it may not be possible to obtain accurate length of the user's waist circumference solely with the magnet pattern information sensed from the magnetic sensor 143. The sensed magnet pattern information may only enable measurement of the circumference of the smart belt 100 worn on the user.

Accordingly, the controller 150 may obtain approximation of the length of the user's waist circumference based on the magnet pattern information sensed from the magnetic sensor 143, and then correct the length of the user's waist circumference to an accurate value, using the tension information obtained from the tension sensor 145.

For example, the controller 150 may correct the approximate length of the waist circumference obtained based on the sensed magnet pattern information, by using measured tension and stored reference tension information. The reference tension information may include tension-based standard table.

The tension-based standard table may be a matching table of the tensions and the waist circumference correction values. According to an exemplary embodiment, the waist circumference correction values included in the tension-based standard table may be calculated in consideration of the body information of the user (e.g., gender, age, height, weight, body type, and so on).

The tension-based standard table may be generated with experimental data. For example, the smart belts 100 may be worn on users with specific genders, ages, heights, and weights, and then circumferences and the tensions of the smart belts 100 may be measured. The correlation between the actual measurement data obtained by actually measuring the lengths of the waist circumferences of the user, and the circumferences and the tensions of the smart belts 100 may then be analyzed. From this, it is possible to obtain a tension and a corresponding waist circumference correction value, and generate a tension-based standard table.

For example, according to the tension-based standard table, when the tension is 0 g, the waist circumference correction value may be '0', and the waist circumference correction value may gradually increase as the tension increases from 0 g. For example, the waist circumference correction value may be '+2 cm' for the tension of 400 g, and the waist circumference correction value may be '+4 cm' for the tension of 700 g.

Meanwhile, when a user wearing the smart belt 100 is sitting or lying, or when the user is deliberately tensioning his or her abdomen, the accurate length of the waist circumference may not be obtained even with the use of the magnet pattern information sensed from the magnetic sensor 143 and the tension information obtained from the tension sensor 145. It would be thus most accurate to measure the waist circumference of the user without the user recognizing about the waist circumference measuring, and with the user in the upright posture with minimum movement. The 'upright posture with minimum movement' herein may refer to a posture of the user who is standing properly and making almost no movement.

Accordingly, using the user motion information sensed through the inertial sensor 141, the controller 150 determines if the user is currently standing properly. When determining that the user is currently standing properly, the controller 150 may obtain the length of the user's waist circumference, using the sensed magnet pattern information and tension information.

According to an exemplary embodiment, the controller 150 may determine the user's moving speed (e.g., walking speed) by using the inertial sensor 141 or the information measured from a separate sensor (not illustrated) that can measure the moving speed of the user, and then perform measurement of the length of the user's waist circumference when the user's movement is equal to or less than a predetermined reference.

Meanwhile, the controller 150 may detect a breathing cycle of the user based on the variations in the tension value measured from the tension sensor 143. Further, the controller 150 may determine whether the detected breathing cycle corresponds to a stable breathing cycle. For example, if the breathing cycle is 3 to 5 seconds and the breathing rate is 12 to 20 times per minute, the controller 150 may determine that the user's breathing is stable. In contrast, when the breathing cycle is less than 3 seconds, and the breathing rate exceeds 20 times per minute, the controller 150 may determine that breathing is unstable.

The controller 150 determines if the user is properly standing, by using the user motion information of the user with stable breathing, and if so, the controller 150 may obtain the length of the user's waist circumference using the sensed magnet pattern information and tension information.

The tension value used for calculating the length of the user's waist circumference may include an average of the tension values measured for a predetermined time, e.g., for a breathing cycle.

Meanwhile, according to an exemplary embodiment, it is still possible to measure the length of the waist circumference even when it is determined that the user is not properly standing. For example, a first length of waist circumference measured when the user is leaning on one side may have an error with the actual length of the user's waist circumference. Accordingly, using the body modeling information of the user, the controller 150 may convert the first length of the waist circumference into a second length of waist circumference that is measured from the user in upright posture with minimum movement.

The body modeling information of the user may be the information obtained by the machine learning technique based on the relationship between the user's posture and the waist circumference. For example, the body modeling information of the user may include a difference in the waist circumferences between sitting and standing, a difference in the waist circumferences between standing upright and leaning on one side, a difference in the waist circumferences between standing and walking, or a difference in the waist circumferences before and after eating, although exemplary embodiments are not limited thereto.

Meanwhile, the controller 150 may correct the tension value measured at the tension sensor 143 according to a moving state of the user. For example, when the first tension value is measured while the user is leaning on one side, the measured first tension value may be corrected to a tension value of the 'upright posture with minimum movement' state.

The controller 150 may transmit the resultant measurement of the user's waist circumference to the host terminal 200 or the server 300 via the communication unit 160 when a certain event occurs. For example, the controller 150 may transmit information on the waist circumference to the host terminal 200 when the event occurs, in which the waist circumference of the user increases by 1 cm. Of course, the controller 150 may transmit the entire information about the waist circumference acquired from the smart belt 100 for a predetermined time period to the host terminal 200 or the server. The information about waist circumference may include information on the length of the waist circumference, and the time during which the waist circumference was measured.

The controller 150 may determine whether the user has abdominal obesity or not based on the measured waist circumference information. To this purpose, user information such as user's age, gender, height, weight, and so on may be provided to the smart belt 100 in advance, and the smart belt 100 may be installed with program to determine whether the user has abdominal obesity or not, by using the user information and the waist circumference information.

The controller 150 may generate user activity information based on the information on whether the smart belt 100 is worn or un-worn, user motion information, magnet pattern information, and tension information. The user activity information may represent the information on the activities that the user does from when the user is awake in the morning until he or she goes to sleep at night. For example, the user activity information may include information on when the user commutes to and from office, overwork information, information on using restrooms, laughing information, drinking information, smoking information, seizure information, fall-accident information, driving time information, information on total time of sitting a day, information on time of going to or from school, information on exercise time, overeating information, and so on. According to an exemplary embodiment, the smart belt 100 may acquire the pattern information (e.g., acceleration value, angular speed value, tension value, and so on) that patterns the movements corresponding to the user activities, and store the pattern information in a memory. By comparing the pattern information stored in the memory with the currently-measured user motion, the smart belt 100 may generate the user activity information. To this purpose, the smart belt 100 may be installed with program to generate the user activity information described above.

The communication unit 160 may perform a communication function to allow data exchange between the smart belt 100 and the host terminal 200, or between the smart belt 100 and the server 300. The communication unit 160 may provide short-distance communication function such as, for example, Bluetooth communication, Bluetooth Low Energy (BLE) communication, Near Field Communication (NFC), WLAN (Wi-Fi) communication, Zigbee communication, Infrared Data Association (IrDA) communication, Wi-Fi Direct (WFD) communication, ultra wideband (UWB) communication, Ant+ communication, and so on.

The memory 170 may store various information, data, and programs associated with the operation of the smart belt 100. The memory 170 may include an internal memory or an external memory. The external memory may be functionally and/or physically coupled with the smart belt 100 via a variety of interfaces. Further, the smart belt 100 may operate a web storage that performs a storage function of the memory 170 on the internet.

The power supply 180 performs a function to supply operation power to the electronic components of the smart belt 100. The power supply 180 may be implemented as a rechargeable battery. Of course, the power supply according to an exemplary embodiment may also be implemented as a disposable battery.

Although the smart belt 100 has been described so far as obtaining measurement of the length of the user's waist circumference, the exemplary embodiments are not limited thereto. Accordingly, the smart belt 100 may perform only the function to provide the measurement information from the inertial sensor 141, the magnetic sensor 143, the tension sensor 145, and so on, to the host device or the server 300 via a communication network. In such embodiment, the host device 200 or the server 300 may obtain the length of the user's waist circumference, using the measurement information from the inertial sensor 131, the magnetic sensor 143, the tension sensor 145, and so on.

Further, the host device 200 or the server 300 may determine whether the user has abdominal obesity or not, or may generate the user activity information, and so on, based on the measurement information from the inertial sensor 141, the magnetic sensor 143, the tension sensor 145, and so on.

The method according to exemplary embodiments may be implemented as a form of program that can be executed with a variety of computer means, and recorded on a computer readable medium. The computer readable medium may include program instructions, data files, data structures, and so on, either individually or in combination. The program instructions recorded on the medium may be specially designed and configured for the purpose of the present disclosure, or may be those that are known and available to those skilled in the computer software field. Examples of the computer readable recording medium include magnetic media such as hard disk, floppy disk and magnetic tape, optical media such as CD-ROM, DVD, and so on, magneto-optical media such as floptical disk, and hardware devices such as ROM, RAM, flash memory, and so on that are specially configured to store and execute program instructions. Examples of the program instructions include not only the machine language codes that are made by the compiler, but also the high-level language codes that can be executed by the computer using interpreter, and so on.

Further, the foregoing exemplary embodiments and advantages are merely exemplary and are not to be construed as limiting the exemplary embodiments. The present teaching can be readily applied to other types of apparatuses. Also, the description of the exemplary embodiments of the present inventive concept is intended to be illustrative, and not to limit the scope of the claims.

What is claimed is:

1. A belt apparatus, comprising:
a strap portion comprising a plurality of magnet patterns;
a first sensor portion configured to sense one of the plurality of magnet patterns while the strap portion is being fastened to a buckle portion;
a clip portion connecting the strap portion with the buckle portion and including a body portion and a cover portion;
an electromagnetic permeable plate attached on an outer side of the cover portion;
a second sensor portion configured to measure a tension exerted on the clip portion while the strap portion is being fastened to the buckle portion, wherein the first sensor portion comprises a magnetic sensor, and the second sensor portion comprises a strain gauge or a force sensing resistor (FSR) sensor, wherein
the body portion includes an attachment surface on which the strain gauge or the FSR sensor is attached, and
the cover portion includes an electromagnetic transmitting window configured to allow the magnetic sensor to sense a magnetic signal generated from the magnet pattern, among the plurality of magnet patterns, that is positioned above the clip portion;
a controller configured to obtain a length of a waist circumference of a user that corresponds to the magnet pattern sensed by the first sensor portion, wherein the controller corrects the length of the waist circumference using a waist circumference correction value corresponding to the measured tension.

2. The belt apparatus of claim 1, wherein the strap portion comprises a plurality of holes corresponding to the plurality of magnet patterns, respectively.

3. The belt apparatus of claim 2, wherein lengths of the waist circumference of the user corresponding to the magnet patterns are determined based on distances from predetermined points of the buckle portion or the clip portion to the holes that correspond to the plurality of magnet patterns, respectively.

4. The belt apparatus of claim 1, further comprising a third sensor portion configured to sense user motion information of a user wearing the belt apparatus,
wherein the controller corrects the tension using the user motion information sensed at the third sensor portion.

5. The belt apparatus of claim 4, wherein the controller measures the length of the waist circumference of the user in a predetermined state, based on the user motion information.

6. The belt apparatus of claim 1, further comprising a memory configured to store a table composed of a waist circumference correction value corresponding to the measured tension.

7. The belt apparatus of claim 1, wherein the plurality of magnet patterns are distinguished from one another according to at least one of: a number of magnets included in the magnet patterns; positions of the magnets; polarities of the magnets; and intensities of the magnets.

* * * * *